(12) United States Patent
Harris et al.

(10) Patent No.: US 10,398,424 B2
(45) Date of Patent: *Sep. 3, 2019

(54) ALIGNMENT TOOL

(71) Applicant: Biomet UK Healthcare Limited, Bridgend (GB)

(72) Inventors: Nick Harris, Leeds (GB); Paul James Kistle, Swindon (GB); Paul Smirthwaite, Bath (GB)

(73) Assignee: Biomet UK Healthcare Limited, Bridgend (GB)

( * ) Notice: Subject to any disclaimer, the term of this patent is extended or adjusted under 35 U.S.C. 154(b) by 429 days.

This patent is subject to a terminal disclaimer.

(21) Appl. No.: 14/858,293

(22) Filed: Sep. 18, 2015

(65) Prior Publication Data

US 2016/0074087 A1    Mar. 17, 2016

Related U.S. Application Data

(63) Continuation of application No. 13/643,216, filed as application No. PCT/GB2011/050846 on Apr. 28, 2011, now Pat. No. 9,138,332.

(30) Foreign Application Priority Data

Apr. 28, 2010    (GB) .................................. 1007062.1

(51) Int. Cl.
*A61B 17/02* (2006.01)
*A61B 17/88* (2006.01)
(Continued)

(52) U.S. Cl.
CPC ............ *A61B 17/025* (2013.01); *A61B 17/17* (2013.01); *A61B 17/8861* (2013.01);
(Continued)

(58) Field of Classification Search
CPC . A61B 17/8866; A61B 17/8869; A61B 17/17; A61B 17/1764; A61B 17/15;
(Continued)

(56) References Cited

U.S. PATENT DOCUMENTS 5,630,820 A * 5/1997 Todd .................... A61B 17/025
606/102
5,669,914 A    9/1997 Eckhoff
(Continued)

FOREIGN PATENT DOCUMENTS

WO    WO2011135372 A1    11/2011

OTHER PUBLICATIONS

"U.S. Appl. No. 13/643,216, Final Office Action dated Mar. 13, 2015", 10 pgs.

(Continued)

*Primary Examiner* — Matthew J Lawson
*Assistant Examiner* — Amy R Sipp
(74) *Attorney, Agent, or Firm* — Schwegman Lundberg & Woessner, P.A.

(57)    ABSTRACT

An alignment tool (2) for a joint is provided comprising a reference member 4 that defines a reference plane R and a distraction member (6). The distraction member (6) comprises first and second distraction arms (70, 72), each of which is independently moveable with respect to the reference member (4) along a movement axis M. The movement axes M, M of the first and second distraction arms (70, 72) are substantially parallel. A kit of parts is also provided comprising an alignment tool (2), a drill guide (200) and a cutting guide (300).

13 Claims, 6 Drawing Sheets

(51) Int. Cl.
*A61F 2/46* (2006.01)
*A61B 17/17* (2006.01)
*A61B 17/15* (2006.01)
*A61B 17/00* (2006.01)
*A61F 2/42* (2006.01)
*A61B 17/56* (2006.01)
*A61B 17/68* (2006.01)

(52) U.S. Cl.
CPC ...... *A61B 17/8866* (2013.01); *A61B 17/8869* (2013.01); *A61F 2/46* (2013.01); *A61F 2/4684* (2013.01); *A61B 17/0206* (2013.01); *A61B 17/15* (2013.01); *A61B 17/1775* (2016.11); *A61B 2017/00407* (2013.01); *A61B 2017/0268* (2013.01); *A61B 2017/565* (2013.01); *A61B 2017/681* (2013.01); *A61F 2/4606* (2013.01); *A61F 2002/4205* (2013.01)

(58) Field of Classification Search
CPC ... A61B 17/154; A61B 17/155; A61B 17/157; A61B 17/02; A61B 17/0206; A61B 17/025; A61B 2017/1775; A61B 2017/681; A61B 2017/0268
USPC ...................... 606/87, 88, 90, 102
See application file for complete search history.

(56) References Cited

U.S. PATENT DOCUMENTS

| | | | |
|---|---|---|---|
| 5,776,137 A | 7/1998 | Katz | |
| 5,860,980 A | 1/1999 | Axelson, Jr. et al. | |
| 5,911,723 A | 6/1999 | Ashby et al. | |
| 8,808,303 B2 | 8/2014 | Stemniski et al. | |
| 9,138,332 B2 | 9/2015 | Harris et al. | |
| 2003/0149378 A1* | 8/2003 | Peabody | A61B 5/1072 600/587 |
| 2004/0097951 A1 | 5/2004 | Steffensmeier | |
| 2004/0249386 A1 | 12/2004 | Faoro | |
| 2004/0249387 A1 | 12/2004 | Faoro | |
| 2005/0256527 A1 | 11/2005 | Delfosse et al. | |
| 2006/0155295 A1* | 7/2006 | Supper | A61B 17/025 606/90 |
| 2007/0293868 A1* | 12/2007 | Delfosse | A61B 17/025 606/88 |
| 2008/0051798 A1 | 2/2008 | Colquhoun et al. | |
| 2009/0138021 A1 | 5/2009 | Colquhoun et al. | |
| 2009/0222089 A1 | 9/2009 | Hauri et al. | |
| 2009/0270869 A1 | 10/2009 | Colquhoun et al. | |
| 2012/0130376 A1 | 5/2012 | Loring et al. | |
| 2012/0259342 A1 | 10/2012 | Chana et al. | |
| 2013/0190765 A1 | 7/2013 | Harris et al. | |

OTHER PUBLICATIONS

"U.S. Appl. No. 13/643,216, Non Final Office Action dated Nov. 5, 2014", 10 pgs.

"U.S. Appl. No. 13/643,216, Notice of Allowance dated May 15, 2015", 7 pgs.

"Canadian Application Serial No. 2,797,338, Office Action dated Feb. 17, 2017", 3 pgs.

"Canadian Application Serial No. 2,797,338, Response filed Jul. 27, 2017 to Office Action dated Feb. 17, 2017", 7 pgs.

* cited by examiner

ALIGNMENT TOOL

This application is a continuation application of U.S. application Ser. No. 13/643,216, filed Apr. 4, 2013, which U.S. application Ser. No. 13/643,216 is a 371 National Stage Application of PCT/GB2011/050846, filed Apr. 28, 2011, which application PCT/GB2011/050846 claims the benefit of priority to United Kingdom Application Serial No. 1007062.1, filed Apr. 28, 2010, the contents of which applications are hereby incorporated by reference in their entireties.

The present invention relates to an alignment tool and particularly but not exclusively to an alignment tool suitable for use in total ankle replacement surgery.

BACKGROUND TO THE INVENTION

It is known to replace diseased or damaged articulating surfaces of a joint with prosthetic components in total or partial joint replacement procedures. During such procedures, it is necessary to balance the tension in the soft tissue structures that support the joint, for example the ligaments and surrounding tissues. In certain cases, it is also desirable to correct for deformities. These deformities may be from a pre-existing injury or condition, or may have developed in the joint in parallel with, and usually as a consequence of, the degradation of the natural articulating surfaces. For example, it is common for an ankle requiring total joint replacement surgery to exhibit a certain degree of varus or valgus deformity. This is where the distal bone of the joint is angled either medially (varus) or laterally (valgus) with respect to the normal joint line. Such deformities can be corrected by placing the joint in the desired anatomical alignment before resecting the distal bone articulating surface in preparation for implantation of the prosthetic component. The bone surface will have worn away, or subsided as a result of trauma, to a greater degree in one compartment or the other (depending on the nature of the deformity). Placing the joint in correct alignment before resecting will therefore cause the removal of a non symmetrical piece of bone, removing less bone from the side that is worn away or subsided in order to restore normal alignment to the joint. In conventional surgical procedures, the joint is placed and held in alignment prior to a distal bone resection by a surgical assistant. The correction for varus or valgus deformities is therefore conducted by eye and the accuracy and repeatability of the resection is dependent upon the surgical assistant holding the limb steady in the correct place.

SUMMARY OF INVENTION

According to the present invention, there is provided an alignment tool for a joint comprising a reference member that defines a reference plane and a distraction member, the distraction member comprising first and second distraction arms, each of which is independently moveable with respect to the reference member along a movement axis, the movement axes of the first and second distraction arms being substantially parallel.

The substantially parallel movement axes of the independently moveable distraction arms enable the alignment tool to differentially distract a bone with respect to a reference plane, thus affording control of the angular alignment of the distracted bone. If used in an ankle joint for example, the alignment tool affords differential distraction of the talus, allowing for correct angular alignment in the coronal plane.

The movement axes of the first and second distraction arms may be substantially perpendicular to the reference plane, which may be particularly advantageous when dealing with a substantially rectangular joint space.

The alignment tool may further comprise a first adjustment means, operatively connecting the first distraction arm and the reference member, and a second adjustment means, operatively connecting the second distraction arm and the reference member.

The reference member may comprise a reference body on which the first and second adjustment means are mounted, and a reference element.

The adjustment means may be mounted on the reference body in an adjustment plane and the reference element may protrude from the adjustment plane along an engagement axis that is angled with respect to the adjustment plane. In this manner, the mechanism of adjustment may be separated spatially from the reference element. This may be particularly advantageous when operating in a small joint space, enabling maximum visibility to be maintained into the joint when the instrument is in place and also ensuring that only those elements of the tool that are required to be within the joint space actually protrude into that space.

The distraction arms may be mounted on the adjustment means in the adjustment plane and may extend from the adjustment plane along axes substantially parallel to the engagement axis of the reference element. In this manner, the distraction arms also protrude into the joint space in use while being mounted on adjustment means that are removed from the joint space and thus not cluttering the space or obscuring the view of the surgeon.

Each adjustment means may comprise an adjustment socket that is mounted on the reference member and receives an adjustment arm, on which a corresponding distraction arm is mounted.

Each adjustment arm may carry a rack and each adjustment socket may carry a pawl for cooperation with the rack. Such a rack and pawl arrangement allows fine control of relative displacement between the arm and socket in which it is received.

The distraction arms may be mounted on the adjustment arms via mounting members.

Each distraction arm may comprise an attachment feature, which may be operable to receive a drill guide. In this manner, the alignment tool may cooperate with further surgical tools to enable drilling and bone resection to be carried out with the joint held in alignment by the alignment tool.

Each attachment feature may comprise an alignment feature, which may be operable to align the drill guide in a plane parallel to the reference plane of the alignment tool. Correct alignment with the reference plane may thus be assured, even with the distraction arms differentially distracted with respect to the reference plane.

The reference element may comprise a trial prosthesis component, which may be a trial tibial component for a total ankle arthroplasty. The trial prosthesis component may be inserted into a joint space such that the reference plane of the alignment tool is the plane in which the articulating surface of an eventually implanted prosthesis component will rest.

According to another aspect of the present invention, there is provided a kit of parts comprising an alignment tool of the first aspect of the present invention and a drill guide, operable to be mounted on the alignment tool. The drill guide may be operable to be received in either one of the attachment features of the first and second distraction arms.

The drill guide may be operable to direct insertion of guide wires. The guide wires may be inserted via inner guide tubes which may be received within outer guide tubes of the drill guide.

The kit of parts may further comprise a cutting guide, operable to be mounted on guide wires directed by the drill guide.

According to another aspect of the present invention, there is provided a method of aligning a joint using a tool comprising a reference member and a distraction member, the distraction member comprising first and second arms, each of which is independently moveable with respect to the reference member, the method comprising:

a) inserting the tool into a joint space;
b) distracting one of the first and second distraction arms relative to the reference member;
c) distracting the other of the first and second distraction arms relative to the reference member; and
d) repeating steps (b) and (c) until the joint is in alignment.

BRIEF DESCRIPTION OF THE DRAWINGS

For a better understanding of the present invention, and to show more clearly how it may be carried into effect, reference will now be made, by way of example, to the following drawings in which.

DETAILED DESCRIPTION OF EMBODIMENTS

Figure 1:
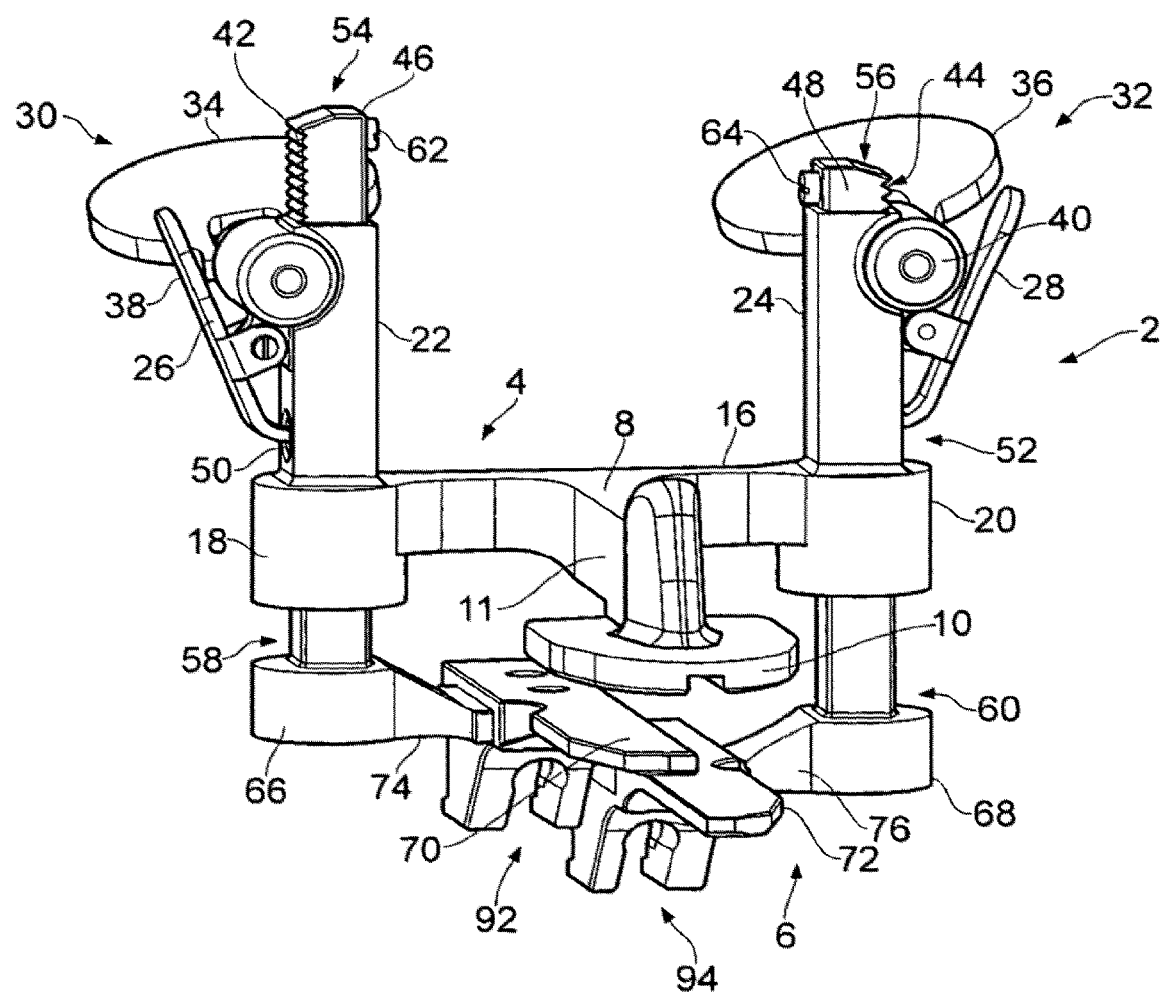
FIG. 1 is a perspective view of an alignment tool, viewed from a front of the tool.
Figure 2:
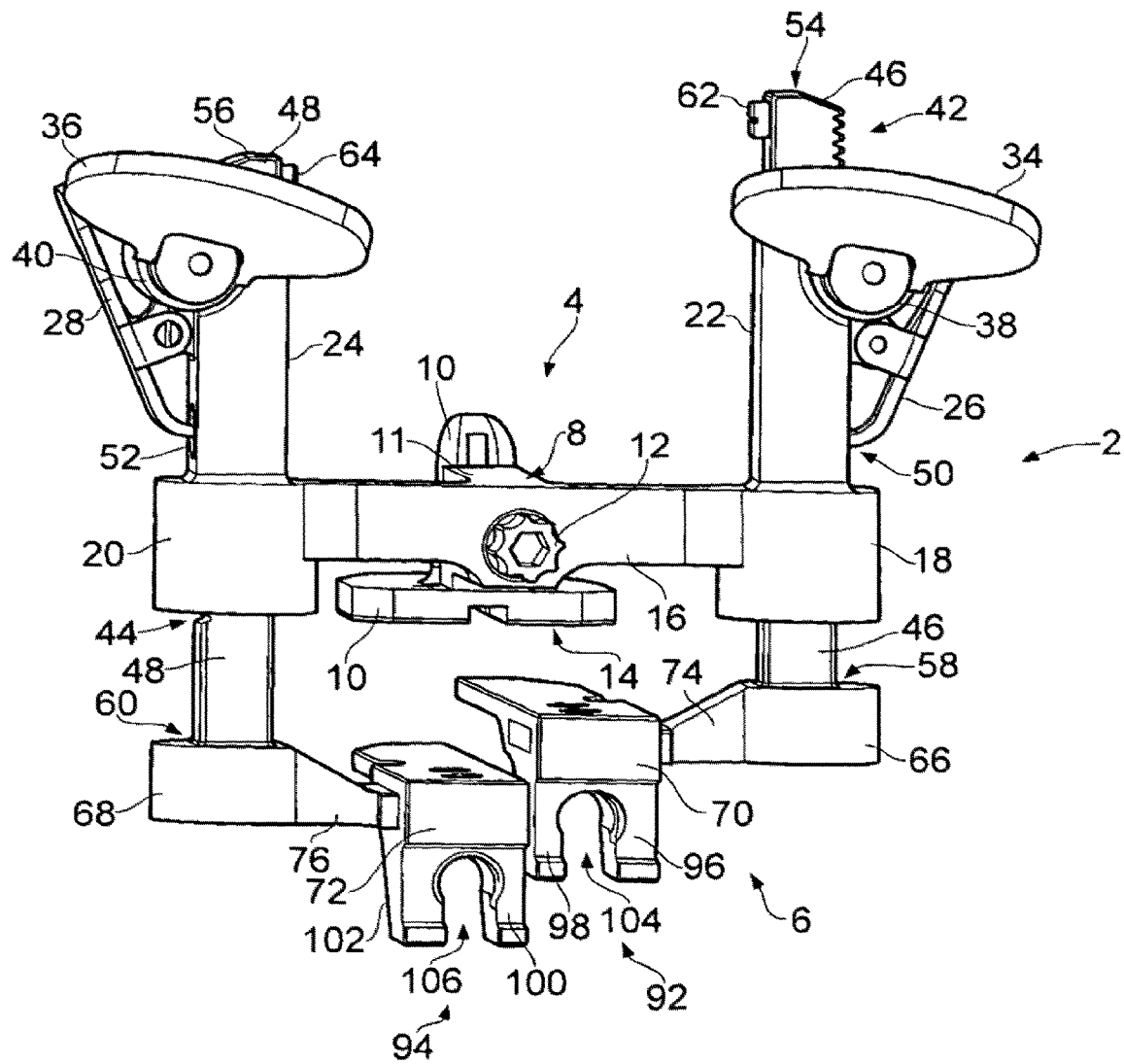
FIG. 2 is another perspective view of the alignment tool of FIG. 1, viewed from a rear of the tool.

With reference to FIGS. 1 to 4, an alignment tool 2 suitable for use in a total ankle replacement procedure comprises a reference member 4 and a distraction member 6. The reference member 4 comprises a T shaped reference body 8 and a reference element 10 in the form of a trial prosthesis component which may be a trial tibial prosthesis component. The T shaped reference body 8 comprises a base 11, that defines an engagement axis E of the tool 2, and a cross bar 16 that extends across the base 11 substantially perpendicularly to the base 11. The base 11 and cross bar 16 are integrally formed. The cross bar 16 lies in an adjustment plane that extends above and below the cross bar 16 such that the engagement axis E of the tool is substantially normal to the adjustment plane.

The reference element 10 is mounted via a threaded rod 12 that extends from a central point of the cross bar 16 of the T shaped reference body 8 through the base 11, such that the reference element 10 is mounted at an end 15 of the base 11 that is remote from the cross bar 16. The reference element 10 comprises an engagement portion 17 and an articulating portion 19 which is integrally formed with the engagement portion 17. The engagement portion 17 comprises a threaded blind bore 21 in which an end of the threaded rod 12 is received to fix the reference element 10 to the reference body 8 of the tool 2. The articulating portion 19 of the reference element 10 comprises a distal planar surface 14 which extends across and defines a reference plane of the tool 2.

At opposite ends of the cross bar 16 of the reference body 8 are adjustment sockets 18, 20, which are integrally formed with the cross bar 16. In an alternative embodiment, the sockets 18, 20 may be fixedly joined to the cross bar 16 in an appropriate manner. Housings 22, 24 extend upwardly (as seen in the Figures) from the sockets 18, 20 in the adjustment plane and spring loaded fingers or pawls 26, 28 are mounted on the housings 22, 24. Rotary drives 30, 32 are also mounted on the housings 22, 24, each drive comprising a handle 34, 36 and a pinion 38, 40. Adjustment arms 46, 48 are received, one in each combination of socket 18, 20 and housing 22, 24. Each adjustment arm 46, 48 comprises a first end 54, 56 (uppermost in the Figures), that protrudes from the associated housing 22, 24, and a second end 58, 60, that protrudes from the associated socket 18, 20.

Each combination of pawl 26, 28 and pinion 38, 40 mounted on the housings 22, 24 engages a respective toothed rack 42, 44 carried on the adjacent adjustment arm 46, 48 which is received within the relevant socket 18, 20 and housing 22, 24. Each pawl 26, 28 is angled to engage the corresponding toothed rack 42, 44 through an opening 50, 52 in the housing 22, 24. The pawls 26, 28 are angled such that relative movement between the adjustment arms 46, 48 and associated housings 22, 24 in a first direction along a movement axis may take place under the action of the rotary drives 30, 32, while relative movement in the opposite direction is opposed. The first direction is a direction in which separation between the second ends 58, 60 of the adjustment arms 46, 48 and the sockets 18, 20 is increased, the second direction being the reverse direction, in which the second ends 58, 60 of the adjustment arms 46, 48 are moved towards and increasingly received within the sockets 18, 20. The rotary drives 30, 32 engage the racks 42, 44 of the adjustment arms 46, 48 via the pinions 38, 40. The pinions 38, 40 mesh with the racks 42, 44 and, under the action of the handles 34, 36, drive linear motion of the adjustment arms 46, 48 in the first direction. If linear motion in the second direction is necessary, the locking action of the pawls 26, 28 may be manually over ridden by depressing the pawls 26, 28 at ends remote from the adjustment arms 46, 48, compressing the springs of the spring loaded pawls 26, 28 and removing the engaging ends of the pawls 26, 28 from engagement with the racks 42, 44. Relative motion between the adjustment arms 46, 48 and the housings 22, 24 may then take place freely in either direction.

Depth stops 62, 64 extend from the first ends 54, 56 of the adjustment arms 46, 48, to prevent the first ends 54, 56 of the adjustment arms 46, 48 being completely received within the housings 22, 24. The depth stops 62, 64 may be in the form of screws that protrude from a face of the adjustment arms 46, 48. Additional depth stops 66, 68 protrude from the second ends 58, 60 of the adjustment arms 46, 48 to prevent the second ends 58, 60 of the adjustment arms 46, 48 being completely received within the sockets 18, 20. The additional depth stops 66, 68 may be in the form of annular shoulders that are operable to engage corresponding annular surfaces of the sockets 18, 20.

First and second distraction arms 70, 72 are mounted one on each second end 58, 60 of the adjustment arms 46, 48. The distraction arms 70, 72 are mounted via mounting members 74, 76 that extend from the additional depth stops 66, 68 at the second ends 58, 60 of the adjustment arms 46, 48. The mounting members 74, 76 extend towards each other, substantially parallel with the cross bar 16 of the reference body 8. The distraction arms 70, 72 are thus mounted substantially below (as seen in the Figures) and in line with the base 11 of the reference body 8 and the reference element 10. The distraction arms 70, 72 extend out of the adjustment plane, in which they are mounted via the mounting members 74, 76, substantially parallel with the engagement axis E defined by the base 11 of the reference body 8. Each distraction arm 70, 72 comprises a lower (as seen in the Figures) engagement surface 78, 80, remote from the reference element 11 and operable to engage a bone surface when the tool 2 is in use. Each distraction arm 70, 72 may be displaced independently relative to the reference body 8 and reference element 11 by turning the appropriate handle 34, 36 and thus driving relative movement between the relevant adjustment arm 46, 48 (on which the distraction arms 70, 72 are mounted) and its associated socket 18, 20 and housing 22, 24 (which are integrally formed with, or at least fixedly joined to the reference body 8).

Each distraction arm 70, 72 carries an attachment feature 92, 94 in the form of two protruding lugs 96, 98, 100, 102, between which a keyhole shaped opening 104, 106 is defined. Each pair of lugs 96, 98, 100, 102 protrudes downwards (as seen in the Figures) from the relevant engagement surface 78, 80 of the associated distraction arm 70, 72 in the region of the mounting members 74, 76 and therefore substantially in the adjustment plane of the tool 2. Each keyhole shaped opening 104, 106 comprises an upper (as seen in the Figures) part cylindrical region that carries an internal thread and defines an approach axis. The two approach axes being substantially parallel to each other and to the engagement axis of the tool. Each of the attachment features 92, 94 comprises an alignment feature in the form of protruding upper 108, 110 and lower 112, 114 lips that extend substantially rearward, away from the distraction members 70, 72. The lower lips 112, 114 are in two parts, a first part on one lug 96, 100 and a second part on the other lug 98, 102 of the relevant pair. The upper 108, 110 and lower 112, 114 lips of each attachment feature 92, 94 comprise facing engagement surfaces that are angled slightly away from one another so as to engage corresponding surfaces on a drill guide 200, as explained in further detail below.

Figure 5:
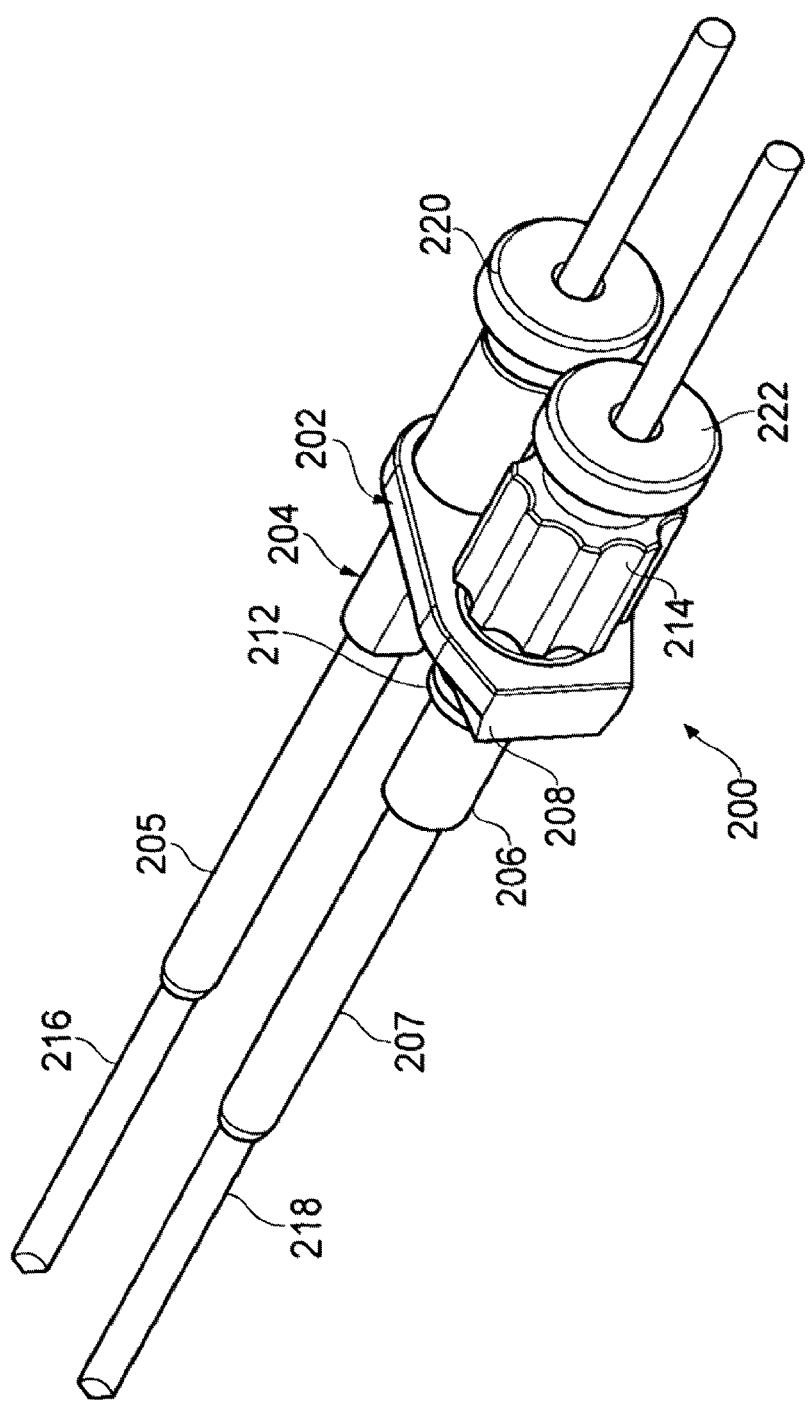
FIG. 5 is a perspective view of a drill guide.

With reference also to FIG. 5, a drill guide 200, suitable for use with the alignment tool, 2 comprises a guide body 202 and two substantially cylindrical outer guide tubes 204, 206 extending though the guide body 202 along parallel axes that define a guide plane. The guide body comprises an alignment feature 208 in the form of a lug 208 that protrudes from an approach face 210 of the guide body, substantially in the region of a dominant one of the outer guide tubes 206. The lug 208 is shaped to fit between and tightly engage the lips 108, 110, 112, 114 of either of the attachment features 92, 94 of the alignment tool 2. The upper and lower regions (as seen in the Figures) of the alignment lug 208 of the drill guide 200 are symmetrical, such that the lug 208 may be received between the lips of either of the attachment features 92, 94 of the alignment tool 2, depending on the orientation of the grill guide 200 with respect to the alignment tool 2. The dominant outer guide tube 206 is rotatable relative to the guide body 202, alignment lug 208 and other outer guide tube 204. The dominant outer guide tube 206 further comprises an attachment feature in the form of an external thread 212 and integral head 214 that is operable to rotate the dominant outer guide tube 206 relative to the guide body 202. The threaded portion 212 of the dominant outer guide tube 206 is dimensioned to be received within the threaded part cylindrical region of the keyhole shaped opening 104, 106 of either of the attachment features 92, 94. Engaging the thread 212 of the dominant outer guide tube 206 into the threaded cylindrical portion of either of the openings 104, 106 brings the lug 208 into close engagement with the lips of the relevant attachment feature 92, 94, thus forcing the drill guide 200 into an alignment where the axis of the dominant outer guide tube 206 is substantially coincident with the approach axis of the attachment feature 92, 94 to which the drill guide 200 is connected.

Figure 3:
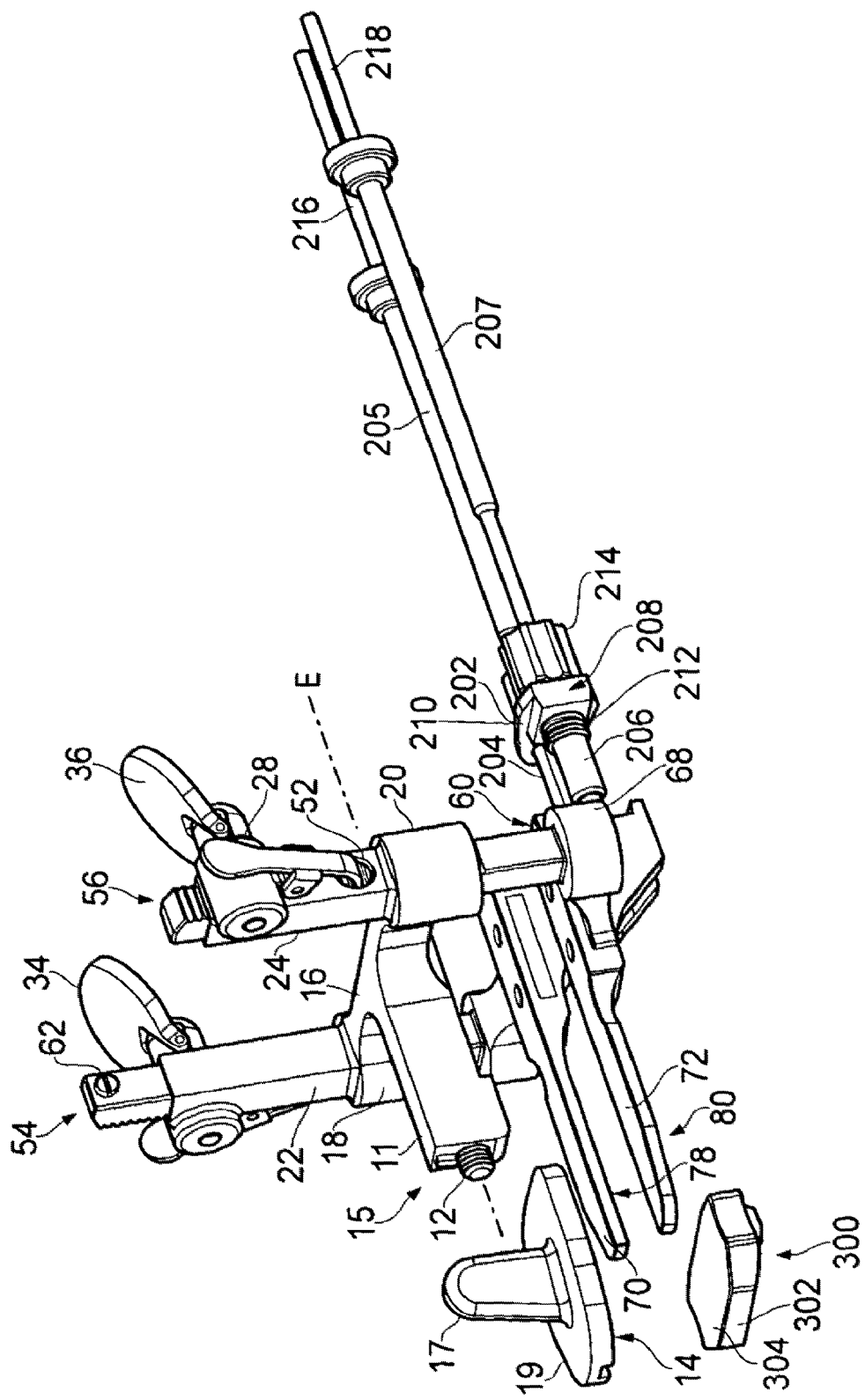
FIG. 3 is an exploded perspective view of a kit of parts comprising an alignment tool, a drill guide and a cutting guide.
Figure 4:
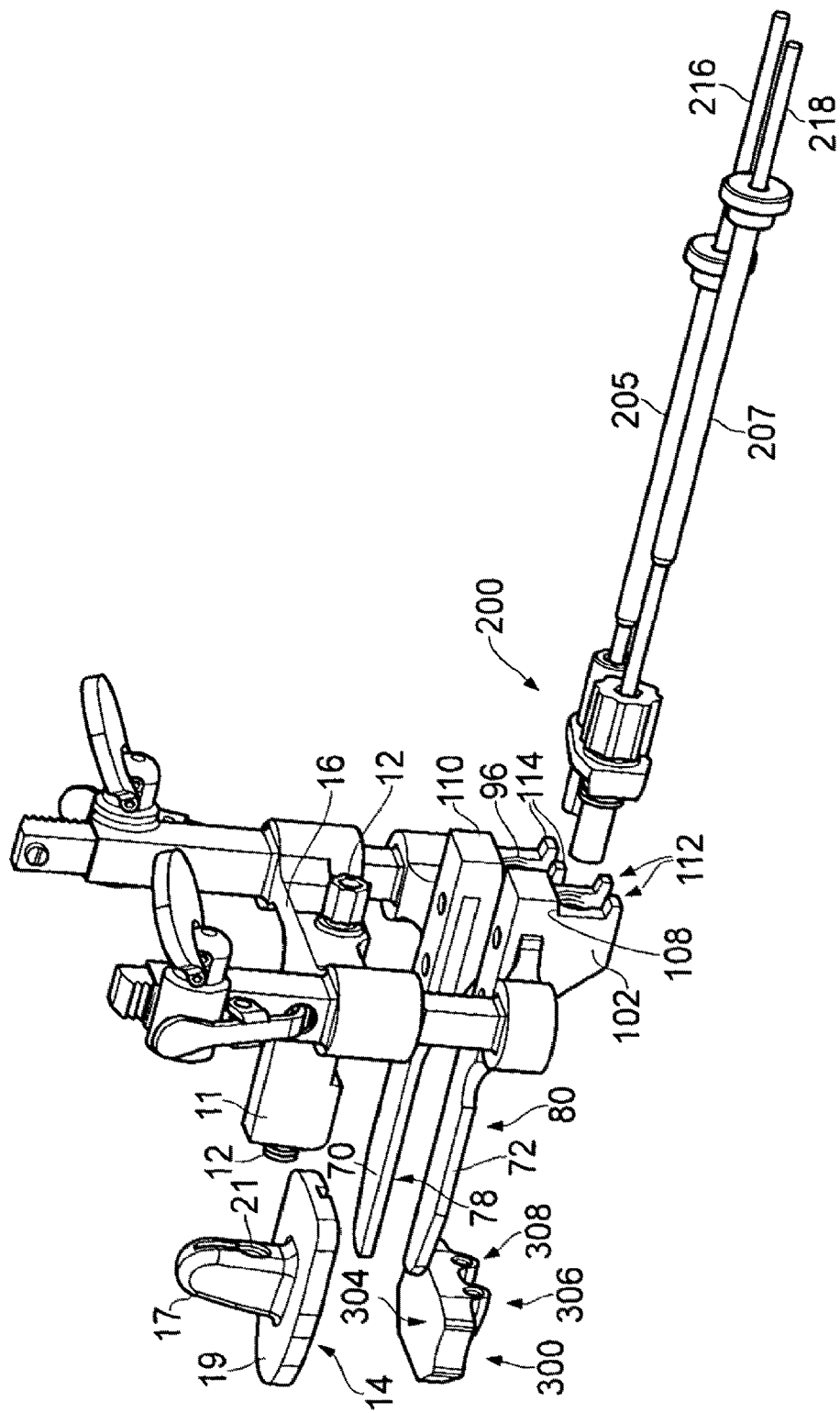
FIG. 4 is another exploded perspective view of the kit of parts of FIG. 3.

The outer guide tubes 204, 206 of the drill guide 200 are operable closely to receive and to direct inner guide tubes 205, 207, which may be inserted down the outer guide tubes 204, 206 using handles 220, 222 until leading edges of the inner guide tubes 205, 207 engage a bone surface. The inner guide tubes 205, 207 are operable to guide a surgical drill in forming bone holes into which guide wires 216, 218 may be inserted. With particular reference to FIGS. 3 and 4, a cutting guide 300 may be mounted on the guide wires 216, 218. The cutting guide comprises a body 302 that carries an upper (as seen in the Figures) cutting guide surface 304, and two mounting lugs 306, 308, through which openings extend. The cutting guide 300 may be mounted on the guide wires 216, 218 via the openings through the mounting lugs 306, 308.

Use of the alignment tool 2, drill guide 200 and cutting guide 300 will now be described with reference to a total ankle replacement operation. It will be appreciated however, that these tools may also be employed in for example total knee replacement surgery or other procedures involving realignment of a joint.

In a total ankle replacement procedure, an incision is first made and soft tissues retracted to give access to the joint. An appropriate tool is then used to guide resection of the distal tibia, so as to prepare the bone surface for implantation of a tibial prosthesis component. Once the distal tibia it prepared, it is then necessary to resect the proximal talus, preferably correcting for any varus or valgus deformity in so doing.

First, the alignment tool 2 of the present invention is assembled with an appropriate trial tibial component 10 fixed to the reference body 8 via the threaded rod 12. The alignment tool is substantially closed by depressing the pawls 26, 28 at their remote ends and thus disengaging the pawls 26, 28 from the racks 42, 44 of the adjustment arms 46, 48 to allow free movement to the adjustment arms 46, 48 in the second direction. The alignment tool 2 is closed when the additional depth stops 66, 68 engage the annular surfaces of the sockets 18, 20, thus bringing the distraction arms 70, 72 into close proximity with the trial tibial prosthesis component 10.

The alignment tool is then inserted into the joint along the engagement axis E. The trial tibial component 10 is substantially implanted into the recess formed in the distal tibia to accept a prosthesis component so that the trial component 10 is substantially in the position that will be occupied by the final prosthesis component once the surgery is complete. With the trial component 10 in place, the distal planar surface 14 of the articulating portion 19 of the trial component 10 defines the reference plane for the tool, the reference plane being the articulating plane of the eventually implanted tibial component. When the trial component is in place, the alignment tool 2 is correctly inserted into the joint, with the two distraction arms 70, 72 symmetrically arranged over the medial and lateral sides of the joint.

Once the trial component 10 is in place, each distraction arm 70, 72 is then moved independently in the first direction (so as to open the alignment tool 2) by rotating the handles 34, 36 of the rotary drives 30, 32. The distraction arms are moved in the first direction until each arm contacts an articulating surface of the talus. Movement of the distraction arms is then continued until the soft tissues of the joint are adequately engaged and the foot is in correct varus/valgus alignment. This will usually involve moving one distraction arm 70, 72 further than the other distraction arm 70, 72, so as to distract the joint differentially and correct for varus/valgus deformities caused by a differentially worn or subsided articulating surface of the talus. This differential distraction effectively rotates the talus and the rest of the foot in the coronal plane, until the foot is correctly aligned with the rest of the lower limb. The locking action of the pawls 26, 28 prevents movement in the second direction (closing the alignment tool 2) and so prevents tension forces in the soft tissues returning the joint to its accustomed misaligned position. Once the soft tissues are engaged, the action of the tension forces in the soft tissues against the locking action of the pawls 26, 28 ensures that the alignment tool 2 remains stably in place with the joint held in the correct varus/valgus alignment.

Figure 6:
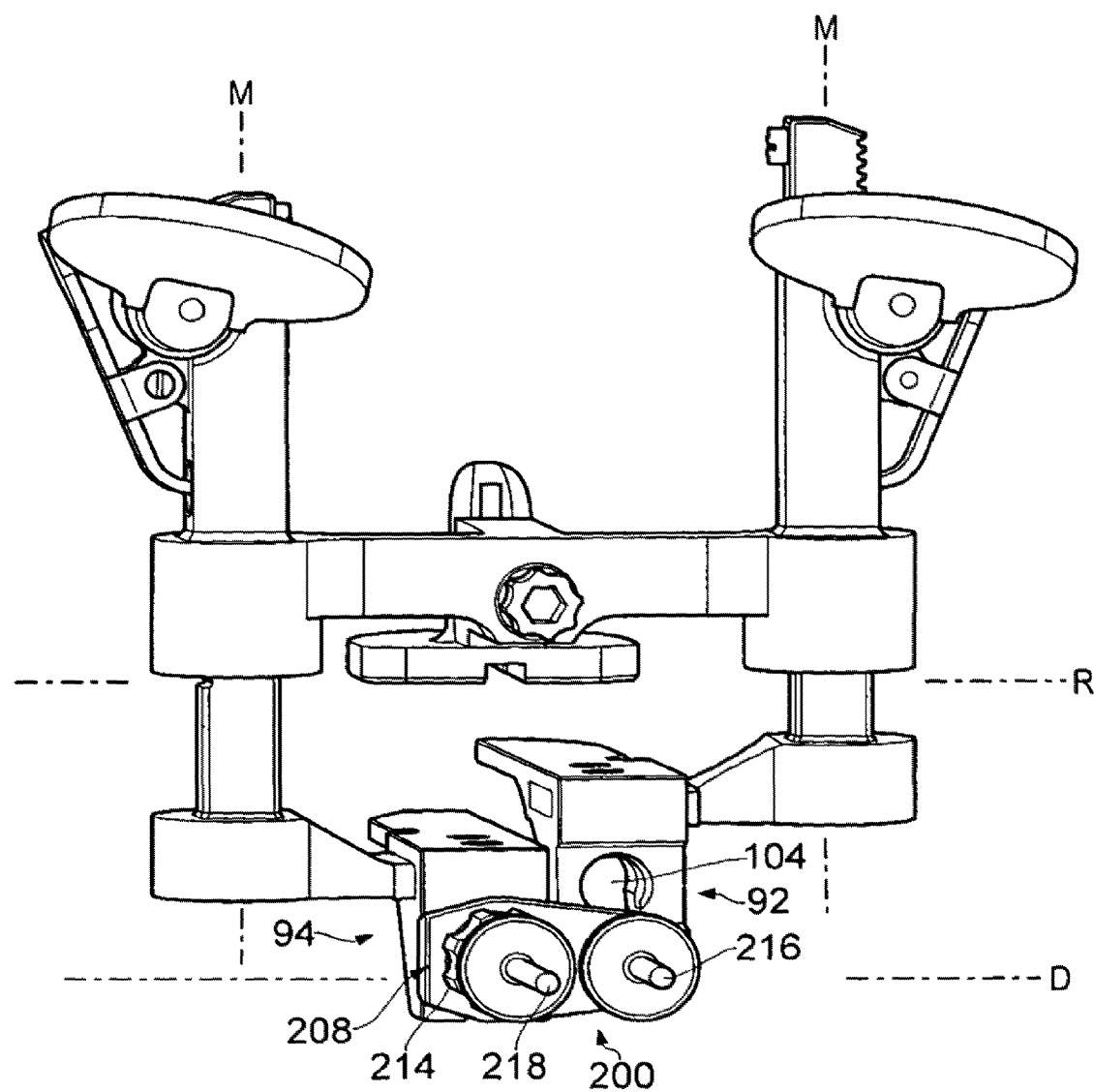
FIG. 6 is a perspective view of the drill guide of FIG. 5 mounted on the alignment tool of FIGS. 1 and 2.

With the joint held in this position by the alignment tool 2, the drill guide 200 is attached to the alignment tool 2 via one of the attachment features 92, 94. The drill guide 200 is oriented such that the dominant outer guide tube 206, carrying the external thread 212 and surrounded by the alignment lug 208 is brought into engagement with the attachment feature of the lower, or more distracted of the two distraction arms 70, 72. This can be seen illustrated in FIG. 6. The thread 212 of the dominant outer guide tube 206 is screwed into engagement with the threaded cylindrical portion of the keyhole shaped opening 104, 106 of the appropriate attachment feature 92, 94. The cooperation of the alignment lug 208 of the drill guide 200 and lips 108, 110 or 112, 114 of the attachment portion 92, 94 ensures that the drill plane D, along which the axes of the outer guide tubes extend, is parallel to the reference plane R of the alignment tool 2, as illustrated in FIG. 6. It will be appreciated that this is made possible, even when the distraction arms that carry the attachment features are no longer parallel following differential distraction of the joint, by the keyhole shaped openings 104, 106 of the attachment features 92, 94. For example, as shown in FIG. 6, with the dominant outer guide tube 206 of the drill guide 200 attached to the lower 94 of the two attachment features 92, 94, the other outer guide tube 204 of the drill guide 200 extends through the lower, substantially rectangular region of the keyhole shaped opening 104 of the other attachment feature 92.

With the drill guide 200 in place, inner guide tubes 205, 207 are inserted into the outer guide tubes 204, 206 until leading edges of the inner guide tubes 205, 207 contact the talar bone surface. A surgical drill bit is then inserted down first one and then the other of the inner guide tubes 205, 207 to drill holes in the talus. The inner guide tubes 205, 207 ensure that the surgical drill bit is supported up to the point of contact with the bone surface. K wires 216, 218 are then inserted down the inner guide tubes 205, 207 and into the drilled holes. Once the K wires are in place, the alignment tool 2 and drill guide 200, including inner guide tubes 205, 207, are removed from the joint, leaving the K wires in position.

The cutting guide 300 is then mounted onto the K wires 216, 218 via the openings in the mounting lugs 306, 308 and is brought into proximity with the talus. The cutting guide 300 is dimensioned such that the planar cutting surface 304 is parallel to the drill plane D in which the K wires 216, 218 extend. As explained above, the drill plane D of the drill guide, through which the K wires are inserted, is parallel to the reference plane of the alignment tool 2, owing to the interaction of the attachment features 92, 94 and the alignment lug of the drill guide 200. The resection guided by the cutting guide 300 is therefore parallel to the reference surface of the trial prosthesis when the foot is in correct varus/valgus alignment, ensuring a rectangular joint gap with the foot in correct alignment, regardless of any differential wear or subsidence on the resected articulating surface of the talus.

Once the talar resection has been made, the cutting guide 300 is removed and any additional cutting and or shaping of the talus may be conducting using appropriate guide tools. The additional tools may be mounted on the K wires 216, 218 as necessary. Once the talus has been sufficiently shaped to receive a talar prosthesis component, the K wires 216, 218 are removed. The tibial and talar prosthesis components, together with an appropriate bearing component may then be implanted in a largely known manner.

The present invention thus provides an alignment tool 2 that enables differential distraction of a joint to be conducted in a controlled and repeatable manner. The interaction of the alignment tool 2, drill guide 200 and cutting guide 300 ensures resection resulting in a rectangular joint gap with the distal bone of the joint in correct alignment with the joint line. The adjustment mechanisms for the tool are removed from the referencing and distracting members, ensuring that the minimum amount of equipment is inserted into the joint space and that the frontal view of the joint is not impaired.

It will be appreciated that such controlled differential distraction may be of considerable assistance in performing surgery on other joints, notably the knee joint.

It will also be appreciated that the alignment tool may be adapted for particular applications. For example, the distraction arms may be curved convex or concave, in order to engage curved bone surfaces. Similarly, the dimensions of the tool may be matched to a particular joint or application as required.

The invention claimed is:

1. An alignment tool for a joint, comprising:
a reference member comprising a reference body;
a trial tibial prosthesis for a total ankle arthroplasty that is sized and structured for implantation into a recess formed in a prepared distal tibia of an ankle joint, the trial tibial prosthesis removably coupled to the reference body in a fixed position and including an engagement portion and an articulating portion integrally formed with the engagement portion, the articulating portion including a distal planar surface that defines a reference plane, wherein upon implantation of the trial tibial prosthesis into the recess formed in the prepared distal tibia the reference plane represents a plane in which an articulating surface of a permanent tibial prosthesis will rest;
a distraction member mounted on the reference body, the distraction member comprising first and second distraction arms spaced below the trial tibial prosthesis, each of which is independently moveable with respect to the reference body along a movement axis, the movement axes of the first and second distraction arms being substantially parallel;
a first adjustment means operatively connecting the first distraction arm and the reference member; and
a second adjustment means operatively connecting the second distraction arm and the reference member;
wherein the first and second adjustment means are mounted on the reference body.

2. A system comprising:
an alignment tool for a joint comprising:
a reference member comprising a reference body;
a reference element removably coupled to the reference body, wherein the reference element defines a reference plane;
a distraction member mounted on the reference body, the distraction member comprising first and second distraction arms, each of which is independently moveable with respect to the reference body along a movement axis, the movement axes of the first and second distraction arms being substantially parallel, wherein each distraction arm of the first and second distraction arms comprises an attachment feature operable to receive a drill guide;
a first adjustment means operatively connecting the first distraction arm and the reference member; and
a second adjustment means operatively connecting the second distraction arm and the reference member;
wherein each adjustment means of the first and second adjustment means comprises an adjustment socket that is mounted on the reference member and receives an adjustment arm, on which a corresponding distraction arm is mounted; and
a drill guide operable to be mounted on the alignment tool, wherein the drill guide is operable to be received in either one of the attachment features of the first and second distraction arms.

3. The system as claimed in claim 2, it wherein the movement axes of the first and second distraction arms are substantially perpendicular to the reference plane.

4. The system as claimed in claim 2, wherein the first and second adjustment means are mounted on the reference body in an adjustment plane and the reference element protrudes from the adjustment plane along an engagement axis that is angled with respect to the adjustment plane.

5. The system as claimed in claim 4, wherein the first and second distraction arms are each mounted on a corresponding one of the first and second adjustment means substantially in the adjustment plane and extend from the adjustment plane along axes substantially parallel to the engagement axis of the reference element.

6. The system as claimed in claim 2, wherein each adjustment arm of the first and second adjustment means carries a rack and each adjustment socket carries a pawl for cooperation with the rack.

7. The system as claimed in claim 2, wherein the first and second distraction arms are each mounted on a corresponding adjustment arm of the first and second adjustment means via mounting members.

8. The system as claimed in claim 2, wherein each attachment feature of the first and second distraction arms comprises an alignment feature operable to align the drill guide in a plane parallel to the reference plane of the alignment tool.

9. The system as claimed in claim 2, wherein the reference element comprises a trial prosthesis component.

10. The system as claimed in claim 9, wherein the reference element comprises a trial tibial component for a total ankle arthroplasty.

11. A system comprising:
an alignment tool for a joint comprising:
a reference member comprising a reference body;
a reference element removably coupled to the reference body, wherein the reference element comprises a trial tibial prosthesis for a total ankle arthroplasty that is sized and structured for implantation into a recess formed in a prepared distal tibia of an ankle joint, the trial tibial prosthesis including an engagement portion and an articulating portion integrally formed with the engagement portion, the articulating portion including a distal planar surface that defines a reference plane, wherein upon implantation of the trial tibial prosthesis into the recess formed in the prepared distal tibia the reference plane represents a plane in which an articulating surface of a permanent tibial prosthesis will rest; and
a distraction member mounted on the reference body, the distraction member comprising first and second distraction arms, each of which is independently moveable with respect to the reference body along a movement axis, the movement axes of the first and second distraction arms being substantially parallel, wherein each distraction arm of the first and second distraction arms comprises an attachment feature operable to receive a drill guide;
a drill guide operable to be mounted on the distraction member of the alignment tool and structured to direct insertion of guide wires; and
a cutting guide operable to be mounted on guide wires directed by the drill guide.

12. The system as claimed in claim 11, wherein the alignment tool further comprises:
a first adjustment means operatively connecting the first distraction arm and the reference member; and
a second adjustment means operatively connecting the second distraction arm and the reference member.

13. The system as claimed in claim 12, wherein the first and second adjustment means are mounted on the reference body.

* * * * *